(12) United States Patent
Ambrosio et al.

(10) Patent No.: US 8,163,974 B2
(45) Date of Patent: *Apr. 24, 2012

(54) BIOCOMPATIBLE WOUND DRESSING

(75) Inventors: Archel Ambrosio, San Antonio, TX (US); Royce W. Johnson, Universal City, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/758,460

(22) Filed: Apr. 12, 2010

(65) Prior Publication Data

US 2010/0249688 A1    Sep. 30, 2010

Related U.S. Application Data

(63) Continuation of application No. 11/657,887, filed on Jan. 25, 2007, now Pat. No. 7,700,819, which is a continuation-in-part of application No. 11/409,116, filed on Apr. 21, 2006, now Pat. No. 7,763,769, which is a continuation of application No. 10/075,743, filed on Feb. 14, 2002, now Pat. No. 7,070,584.

(60) Provisional application No. 60/269,657, filed on Feb. 16, 2001.

(51) Int. Cl.
*A61F 13/00* (2006.01)
*A61M 35/00* (2006.01)

(52) U.S. Cl. .............. 602/48; 602/41; 602/42; 604/289; 604/290

(58) Field of Classification Search .................. 602/1, 2, 602/41–42, 46, 48, 57, 58; 604/289–291, 604/304–308; 128/897

See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

AU    550575 A1    8/1982

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).

(Continued)

*Primary Examiner* — Kim M Lewis
(74) *Attorney, Agent, or Firm* — SNR Denton US LLP

(57) ABSTRACT

A multi-layer reduced pressure delivery apparatus is provided for applying reduced pressure tissue treatment to a tissue site. The multi-layer apparatus includes a tissue contact layer, a release layer, and a manifold layer. The tissue contact layer includes a scaffold adapted to contact the tissue site, the release layer includes a water-soluble polymer and a plurality of flow channels, and the manifold layer includes a distribution manifold. The release layer is positioned between the tissue contact layer and the manifold layer to allow easy release of the manifold layer from the tissue contact layer following the administration of reduced pressure tissue treatment.

77 Claims, 4 Drawing Sheets

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,118,470 A | 10/1978 | Casey et al. |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,595,713 A | 6/1986 | St. John |
| 4,605,399 A | 8/1986 | Weston et al. |
| 4,608,041 A | 8/1986 | Nielsen |
| 4,614,794 A | 9/1986 | Easton et al. |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,837,015 A | 6/1989 | Olsen |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,904,260 A | 2/1990 | Ray et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,077,049 A | 12/1991 | Dunn et al. |
| 5,085,861 A | 2/1992 | Gerhart et al. |
| 5,086,170 A | 2/1992 | Luheshi et al. |
| 5,092,858 A | 3/1992 | Benson et al. |
| 5,100,396 A | 3/1992 | Zamierowski |
| 5,102,983 A | 4/1992 | Kennedy |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,256,418 A | 10/1993 | Kemp et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,303,719 A | 4/1994 | Wilk et al. |
| 5,324,519 A | 6/1994 | Dunn et al. |
| 5,342,376 A | 8/1994 | Ruff |
| 5,344,415 A | 9/1994 | DeBusk et al. |
| 5,358,494 A | 10/1994 | Svedman |
| 5,368,859 A | 11/1994 | Dunn et al. |
| 5,437,622 A | 8/1995 | Carion |
| 5,437,651 A | 8/1995 | Todd et al. |
| 5,447,725 A | 9/1995 | Damani et al. |
| 5,449,383 A | 9/1995 | Chatelier et al. |
| 5,487,897 A | 1/1996 | Polson et al. |
| 5,527,293 A | 6/1996 | Zamierowski |
| 5,549,584 A | 8/1996 | Gross |
| 5,556,375 A | 9/1996 | Ewall |
| 5,578,662 A | 11/1996 | Bennett et al. |
| 5,599,552 A | 2/1997 | Dunn et al. |
| 5,607,388 A | 3/1997 | Ewall |
| 5,621,035 A | 4/1997 | Lyles et al. |
| 5,622,707 A | 4/1997 | Dorigatti et al. |
| 5,629,186 A | 5/1997 | Yasukawa et al. |
| 5,636,643 A | 6/1997 | Argenta et al. |
| 5,645,081 A | 7/1997 | Argenta et al. |
| 5,674,192 A | 10/1997 | Sahatjian et al. |
| 5,711,957 A | 1/1998 | Patat et al. |
| 5,711,958 A | 1/1998 | Cohn et al. |
| 5,717,030 A | 2/1998 | Dunn et al. |
| 5,759,570 A | 6/1998 | Arnold |
| 5,780,281 A | 7/1998 | Yasukawa et al. |
| 5,795,584 A | 8/1998 | Totakura et al. |
| 5,824,335 A | 10/1998 | Dorigatti et al. |
| 5,834,188 A | 11/1998 | Harada et al. |
| 5,902,874 A | 5/1999 | Roby et al. |
| 5,902,875 A | 5/1999 | Roby et al. |
| 5,914,387 A | 6/1999 | Roby et al. |
| 5,932,716 A | 8/1999 | Sampath |
| 5,951,295 A | 9/1999 | Lyles et al. |
| 5,997,568 A | 12/1999 | Liu |
| 6,001,117 A | 12/1999 | Huxel et al. |
| 6,040,431 A | 3/2000 | Keck et al. |
| 6,071,267 A | 6/2000 | Zamierowski |
| 6,083,524 A | 7/2000 | Sawhney et al. |
| 6,087,479 A | 7/2000 | Stamler et al. |
| 6,090,544 A | 7/2000 | Harada et al. |
| 6,093,388 A | 7/2000 | Ferguson |
| 6,103,491 A | 8/2000 | Sampath |
| 6,110,460 A | 8/2000 | Sampath |
| 6,135,116 A | 10/2000 | Vogel et al. |
| 6,136,333 A | 10/2000 | Cohn et al. |
| 6,187,047 B1 | 2/2001 | Kwan et al. |
| 6,200,606 B1 | 3/2001 | Peterson et al. |
| 6,241,747 B1 | 6/2001 | Ruff |
| 6,255,277 B1 | 7/2001 | Stamler et al. |
| 6,287,316 B1 | 9/2001 | Agarwal et al. |
| 6,316,523 B1 | 11/2001 | Hyon et al. |
| 6,345,623 B1 | 2/2002 | Heaton et al. |
| 6,352,709 B1 | 3/2002 | Stamler et al. |
| 6,383,478 B1 | 5/2002 | Prokop et al. |
| 6,387,391 B1 | 5/2002 | Shikinami et al. |
| 6,392,974 B2 | 5/2002 | Shyu |
| 6,395,293 B2 | 5/2002 | Polson et al. |
| 6,407,060 B1 | 6/2002 | Charette et al. |
| 6,471,978 B1 | 10/2002 | Stamler et al. |
| 6,479,643 B1 | 11/2002 | Keck et al. |
| 6,488,643 B1 | 12/2002 | Tumey et al. |
| 6,491,693 B1 | 12/2002 | Lytinas |
| 6,493,568 B1 | 12/2002 | Bell et al. |
| 6,498,142 B1 | 12/2002 | Sampath et al. |
| 6,514,534 B1 | 2/2003 | Sawhney |
| 6,521,223 B1 | 2/2003 | Calias et al. |
| 6,553,998 B2 | 4/2003 | Heaton et al. |
| 6,565,871 B2 | 5/2003 | Roser et al. |
| 6,566,345 B2 | 5/2003 | Miller et al. |

| Patent No. | Date | Inventor |
|---|---|---|
| 6,579,533 B1 | 6/2003 | Törmälä et al. |
| 6,599,518 B2 | 7/2003 | Oster et al. |
| 6,692,773 B2 | 2/2004 | Burrell et al. |
| 6,696,499 B1 | 2/2004 | Cohn et al. |
| 6,713,083 B1 | 3/2004 | McGregor et al. |
| 6,726,923 B2 | 4/2004 | Iyer et al. |
| 6,780,890 B2 | 8/2004 | Bassler et al. |
| 6,814,079 B2 | 11/2004 | Heaton et al. |
| 6,893,424 B2 | 5/2005 | Shchervinsky |
| 6,913,589 B2 | 7/2005 | Dextradeur et al. |
| 6,939,568 B2 | 9/2005 | Burrell et al. |
| 6,989,156 B2 | 1/2006 | Gillis |
| 7,008,647 B2 | 3/2006 | Burrell et al. |
| 7,025,990 B2 | 4/2006 | Sawhney |
| 7,041,868 B2 | 5/2006 | Greene et al. |
| 7,052,708 B2 | 5/2006 | O'Leary |
| 7,070,584 B2 | 7/2006 | Johnson |
| 7,074,412 B2 | 7/2006 | Weber |
| 7,166,570 B2 | 1/2007 | Hunter et al. |
| 7,182,758 B2 | 2/2007 | McCraw |
| 7,201,925 B2 | 4/2007 | Gillis |
| 7,202,281 B2 | 4/2007 | Cohn et al. |
| 7,216,651 B2 | 5/2007 | Argenta et al. |
| 7,241,736 B2 | 7/2007 | Hunter et al. |
| 7,244,444 B2 | 7/2007 | Bates |
| 7,255,881 B2 | 8/2007 | Gillis et al. |
| 7,265,098 B2 | 9/2007 | Miller et al. |
| 7,294,334 B1 | 11/2007 | Michal et al. |
| 7,294,350 B2 | 11/2007 | Marraccini |
| 7,306,903 B1 | 12/2007 | Sampath et al. |
| 7,326,426 B2 | 2/2008 | Nathan et al. |
| 7,342,048 B2 | 3/2008 | Miyaji et al. |
| 7,351,250 B2 | 4/2008 | Zamierowski |
| 7,361,168 B2 | 4/2008 | Makower et al. |
| 7,390,497 B2 | 6/2008 | DesNoyer et al. |
| 7,700,819 B2 * | 4/2010 | Ambrosio et al. ............... 602/48 |
| 7,763,769 B2 | 7/2010 | Johnson et al. |
| 2001/0000728 A1 | 5/2001 | Sawhney et al. |
| 2001/0009662 A1 | 7/2001 | Cohn et al. |
| 2001/0012511 A1 | 8/2001 | Bezwada et al. |
| 2001/0041743 A1 | 11/2001 | Offenbacher et al. |
| 2001/0043943 A1 | 11/2001 | Coffey |
| 2001/0055622 A1 | 12/2001 | Burrell et al. |
| 2002/0001608 A1 | 1/2002 | Polson et al. |
| 2002/0010150 A1 | 1/2002 | Cortese et al. |
| 2002/0028181 A1 | 3/2002 | Miller et al. |
| 2002/0055721 A1 | 5/2002 | Palasis et al. |
| 2002/0072798 A1 | 6/2002 | Riesle et al. |
| 2002/0077661 A1 | 6/2002 | Saadat |
| 2002/0107223 A1 | 8/2002 | Oster et al. |
| 2002/0115951 A1 | 8/2002 | Norstrem et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0193336 A1 | 12/2002 | Elkins et al. |
| 2003/0003127 A1 | 1/2003 | Brown et al. |
| 2003/0027744 A1 | 2/2003 | Dana et al. |
| 2003/0028140 A1 | 2/2003 | Greff |
| 2003/0039697 A1 | 2/2003 | Zhao et al. |
| 2003/0060752 A1 | 3/2003 | Bergheim et al. |
| 2003/0072783 A1 | 4/2003 | Stamler et al. |
| 2003/0077242 A1 | 4/2003 | Sawhney |
| 2003/0077311 A1 | 4/2003 | Vyakarnam et al. |
| 2003/0096734 A1 | 5/2003 | Dehazya et al. |
| 2003/0108511 A1 | 6/2003 | Sawhney |
| 2003/0113359 A1 | 6/2003 | Iyer et al. |
| 2003/0118651 A1 | 6/2003 | Jampani et al. |
| 2003/0125230 A1 | 7/2003 | Cohen et al. |
| 2003/0135148 A1 | 7/2003 | Dextradeur et al. |
| 2003/0152522 A1 | 8/2003 | Miller et al. |
| 2003/0152546 A1 | 8/2003 | Shalaby |
| 2003/0211793 A1 | 11/2003 | Bell et al. |
| 2003/0232087 A1 | 12/2003 | Lawin et al. |
| 2004/0001872 A1 | 1/2004 | Shih et al. |
| 2004/0006311 A1 | 1/2004 | Shchervinsky |
| 2004/0023842 A1 | 2/2004 | Pathak et al. |
| 2004/0037836 A1 | 2/2004 | Stamler et al. |
| 2004/0039415 A1 | 2/2004 | Zamierowski |
| 2004/0063606 A1 | 4/2004 | Chu et al. |
| 2004/0063612 A1 | 4/2004 | Yalpani |
| 2004/0093026 A1 | 5/2004 | Weidenhagen et al. |
| 2004/0097402 A1 | 5/2004 | Bassler et al. |
| 2004/0101564 A1 | 5/2004 | Rioux et al. |
| 2004/0127475 A1 | 7/2004 | New et al. |
| 2004/0127843 A1 | 7/2004 | Tu et al. |
| 2004/0142888 A1 | 7/2004 | Manne et al. |
| 2004/0156819 A1 | 8/2004 | Cohn et al. |
| 2004/0180829 A1 | 9/2004 | Bassler et al. |
| 2004/0197409 A1 | 10/2004 | Iyer et al. |
| 2004/0208845 A1 | 10/2004 | Michal et al. |
| 2004/0213756 A1 | 10/2004 | Michal et al. |
| 2004/0217146 A1 | 11/2004 | Beck |
| 2004/0253203 A1 | 12/2004 | Hossainy et al. |
| 2004/0265475 A1 | 12/2004 | Hossainy et al. |
| 2005/0008609 A1 | 1/2005 | Cohn et al. |
| 2005/0019303 A1 | 1/2005 | Tsai et al. |
| 2005/0027265 A1 | 2/2005 | Maki et al. |
| 2005/0042197 A1 | 2/2005 | Shalaby |
| 2005/0048121 A1 | 3/2005 | East et al. |
| 2005/0063937 A1 | 3/2005 | Li et al. |
| 2005/0106119 A1 | 5/2005 | Brandom et al. |
| 2005/0107756 A1 | 5/2005 | McCraw |
| 2005/0112087 A1 | 5/2005 | Musso et al. |
| 2005/0112186 A1 | 5/2005 | Devore et al. |
| 2005/0129624 A1 | 6/2005 | Burrell et al. |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0158274 A1 | 7/2005 | Hunter et al. |
| 2005/0159364 A1 | 7/2005 | Cooper |
| 2005/0159697 A1 | 7/2005 | Dextradeur et al. |
| 2005/0163822 A1 | 7/2005 | Shirahama et al. |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0175667 A1 | 8/2005 | Carlyle |
| 2005/0177190 A1 | 8/2005 | Zamierowski |
| 2005/0182445 A1 | 8/2005 | Zamierowski |
| 2005/0186247 A1 | 8/2005 | Hunter et al. |
| 2005/0187268 A1 | 8/2005 | Von Rechenberg et al. |
| 2005/0191248 A1 | 9/2005 | Hunter et al. |
| 2005/0208094 A1 | 9/2005 | Armitage et al. |
| 2005/0234510 A1 | 10/2005 | Zamierowski |
| 2005/0238683 A1 | 10/2005 | Adhikari et al. |
| 2005/0240147 A1 | 10/2005 | Makower et al. |
| 2005/0240220 A1 | 10/2005 | Zamierowski |
| 2005/0244363 A1 | 11/2005 | Hossainy et al. |
| 2005/0245906 A1 | 11/2005 | Makower et al. |
| 2005/0249697 A1 | 11/2005 | Uhrich et al. |
| 2005/0255079 A1 | 11/2005 | Santerre et al. |
| 2005/0255082 A1 | 11/2005 | Santerre et al. |
| 2005/0266086 A1 | 12/2005 | Sawhney |
| 2005/0271617 A1 | 12/2005 | Shirahama et al. |
| 2005/0277577 A1 | 12/2005 | Hunter et al. |
| 2006/0024266 A1 | 2/2006 | Brandom et al. |
| 2006/0035861 A1 | 2/2006 | Berg et al. |
| 2006/0051394 A1 | 3/2006 | Moore et al. |
| 2006/0052743 A1 | 3/2006 | Reynolds |
| 2006/0057179 A1 | 3/2006 | Giroux |
| 2006/0067908 A1 | 3/2006 | Ding |
| 2006/0115449 A1 | 6/2006 | Pacetti |
| 2006/0120994 A1 | 6/2006 | Cotton et al. |
| 2006/0135912 A1 | 6/2006 | Chernomorsky et al. |
| 2006/0140904 A1 | 6/2006 | Wellisz et al. |
| 2006/0142736 A1 | 6/2006 | Hissink et al. |
| 2006/0147409 A1 | 7/2006 | Pathak et al. |
| 2006/0147412 A1 | 7/2006 | Hossainy et al. |
| 2006/0148958 A1 | 7/2006 | Haraguchi et al. |
| 2006/0153796 A1 | 7/2006 | Fitz |
| 2006/0177416 A1 | 8/2006 | Turnell et al. |
| 2006/0177417 A1 | 8/2006 | Musso et al. |
| 2006/0188545 A1 | 8/2006 | Hadba |
| 2006/0198815 A1 | 9/2006 | Barker et al. |
| 2006/0216323 A1 | 9/2006 | Knaack et al. |
| 2006/0240063 A9 | 10/2006 | Hunter et al. |
| 2006/0240064 A9 | 10/2006 | Hunter et al. |

| | | | | | | |
|---|---|---|---|---|---|---|
| 2006/0251612 | A1 | 11/2006 | Kotzev et al. | GB | 2 195 255 A | 4/1988 |
| 2006/0263330 | A1 | 11/2006 | Emeta et al. | GB | 2 197 789 A | 6/1988 |
| 2006/0280720 | A1 | 12/2006 | Fitz et al. | GB | 2 220 357 A | 1/1990 |
| 2006/0286063 | A1 | 12/2006 | Shebuski et al. | GB | 2 235 877 A | 3/1991 |
| 2006/0292077 | A1 | 12/2006 | Zhao | GB | 2 333 965 A | 8/1999 |
| 2007/0014752 | A1 | 1/2007 | Roy et al. | GB | 2 329 127 B | 8/2000 |
| 2007/0025955 | A1 | 2/2007 | Lowinger et al. | GB | 2415382 A | 12/2005 |
| 2007/0116666 | A1 | 5/2007 | Cohn et al. | JP | 4129536 | 4/1992 |
| 2007/0128152 | A1 | 6/2007 | Hadba et al. | SG | 71559 | 4/2002 |
| 2007/0128153 | A1 | 6/2007 | Hadba et al. | WO | WO 80/02182 | 10/1980 |
| 2007/0128154 | A1 | 6/2007 | Hadba et al. | WO | WO 86/04235 A1 | 7/1986 |
| 2007/0128155 | A1 | 6/2007 | Seyedin et al. | WO | WO 87/04626 | 8/1987 |
| 2007/0218124 | A1 | 9/2007 | Devore et al. | WO | WO 90/10424 | 9/1990 |
| 2007/0219497 | A1 | 9/2007 | Johnson et al. | WO | WO 91/01126 A1 | 2/1991 |
| 2007/0225663 | A1 | 9/2007 | Watt et al. | WO | WO 93/09727 | 5/1993 |
| 2007/0237750 | A1 | 10/2007 | Naughton | WO | WO 94/20041 | 9/1994 |
| 2007/0248643 | A1 | 10/2007 | Devore et al. | WO | WO 94/22455 A1 | 10/1994 |
| 2007/0248676 | A1 | 10/2007 | Stamler et al. | WO | WO 94/28935 A1 | 12/1994 |
| 2007/0265585 | A1 | 11/2007 | Joshi et al. | WO | WO 96/05873 | 2/1996 |
| 2007/0265586 | A1 | 11/2007 | Joshi et al. | WO | WO 96/17606 A1 | 6/1996 |
| 2007/0275033 | A9 | 11/2007 | Moore et al. | WO | WO 96/35416 A1 | 11/1996 |
| 2007/0280899 | A1 | 12/2007 | Williams et al. | WO | WO 96/38136 A1 | 12/1996 |
| 2008/0003253 | A1 | 1/2008 | Clauser | WO | WO 96/40771 A1 | 12/1996 |
| 2008/0003299 | A1 | 1/2008 | Trotter et al. | WO | WO 97/02794 A1 | 1/1997 |
| 2008/0004368 | A1 | 1/2008 | Wang et al. | WO | WO 97/05241 A2 | 2/1997 |
| 2008/0004578 | A1 | 1/2008 | Hixon et al. | WO | WO 97/05285 A2 | 2/1997 |
| 2008/0014170 | A1 | 1/2008 | Hnojewyj et al. | WO | WO 97/18007 | 5/1997 |
| 2008/0014286 | A1 | 1/2008 | Gillis et al. | WO | WO 97/34626 A1 | 9/1997 |
| 2008/0019969 | A1 | 1/2008 | Gorman | WO | WO 97/36553 A1 | 10/1997 |
| 2008/0031918 | A1 | 2/2008 | Lawin et al. | WO | WO 97/37002 A1 | 10/1997 |
| 2008/0031919 | A1 | 2/2008 | Henson et al. | WO | WO 98/02171 A1 | 1/1998 |
| 2008/0057024 | A1 | 3/2008 | Zhang et al. | WO | WO 99/02168 A1 | 1/1999 |
| 2008/0063620 | A1 | 3/2008 | Cohn et al. | WO | WO 99/13793 | 3/1999 |
| 2008/0069865 | A1 | 3/2008 | Southard et al. | WO | WO 00/09087 A1 | 2/2000 |
| 2008/0071234 | A1 | 3/2008 | Kelch et al. | WO | WO 00/45804 A2 | 8/2000 |
| 2008/0086110 | A1 | 4/2008 | Galdonik et al. | WO | WO 00/56374 A1 | 9/2000 |
| 2008/0095736 | A1 | 4/2008 | Pathak et al. | WO | WO 01/12203 A1 | 2/2001 |
| 2008/0097295 | A1 | 4/2008 | Makower et al. | WO | WO 01/30386 A1 | 5/2001 |
| 2008/0112921 | A1 | 5/2008 | Chamness | WO | WO 01/51054 A2 | 7/2001 |
| 2008/0154250 | A1 | 6/2008 | Makower et al. | WO | WO 01/70199 A1 | 9/2001 |
| 2008/0160064 | A1 | 7/2008 | Capelli et al. | WO | WO 01/82863 A2 | 11/2001 |
| | | | | WO | WO 01/82937 A1 | 11/2001 |
| | FOREIGN PATENT DOCUMENTS | | | WO | WO 01/85664 A2 | 11/2001 |
| AU | 745271 | | 4/1999 | WO | WO 02/09729 A2 | 2/2002 |
| AU | 755496 | | 2/2002 | WO | WO 02/062335 A2 | 8/2002 |
| CA | 2005436 | | 6/1990 | WO | WO 02/072020 A2 | 9/2002 |
| DE | 26 40 413 A1 | | 3/1978 | WO | WO 02/085384 A2 | 10/2002 |
| DE | 43 06 478 A1 | | 9/1994 | WO | WO 02/085385 A2 | 10/2002 |
| DE | 295 04 378 U1 | | 10/1995 | WO | WO 02/085386 A2 | 10/2002 |
| DE | 69723429 T2 | | 4/2004 | WO | WO 02/085387 A2 | 10/2002 |
| DE | 60210441 T2 | | 11/2006 | WO | WO 03/028590 A1 | 4/2003 |
| EP | 0100148 A1 | | 2/1984 | WO | WO 03/066705 A1 | 8/2003 |
| EP | 0117632 A2 | | 9/1984 | WO | WO 03/068245 A1 | 8/2003 |
| EP | 0161865 A2 | | 11/1985 | WO | WO 2004/002456 A1 | 1/2004 |
| EP | 0317780 A1 | | 5/1989 | WO | WO 2004/009147 A1 | 1/2004 |
| EP | 0358302 A2 | | 3/1990 | WO | WO 2004/009227 A2 | 1/2004 |
| EP | 0484387 | | 2/1991 | WO | WO 2004/015130 A2 | 2/2004 |
| EP | 0955969 | | 1/1997 | WO | WO 2004/019876 A2 | 3/2004 |
| EP | 0842268 | | 2/1997 | WO | WO 2004/020011 A1 | 3/2004 |
| EP | 0894004 | | 9/1997 | WO | WO 2004/028548 A2 | 4/2004 |
| EP | 0939639 | | 1/1998 | WO | WO 2004/037311 A2 | 5/2004 |
| EP | 1014998 | | 1/1999 | WO | WO 2004/037334 A1 | 5/2004 |
| EP | 0943299 A1 | | 9/1999 | WO | WO 2004/041346 A1 | 5/2004 |
| EP | 1038538 A1 | | 9/2000 | WO | WO 2004/091592 A2 | 10/2004 |
| EP | 1244725 | | 6/2001 | WO | WO 2004/110347 A2 | 12/2004 |
| EP | 1208850 A1 | | 5/2002 | WO | WO 2005/027957 A1 | 3/2005 |
| EP | 1325753 A2 | | 7/2003 | WO | WO 2005/039489 A1 | 5/2005 |
| EP | 1327460 A2 | | 7/2003 | WO | WO 2005/039537 A1 | 5/2005 |
| EP | 1383522 | | 1/2004 | WO | WO 2005/041987 A1 | 5/2005 |
| EP | 1018967 B1 | | 8/2004 | WO | WO 2005/044285 A1 | 5/2005 |
| EP | 1457499 A1 | | 9/2004 | WO | WO 2005/046746 A2 | 5/2005 |
| EP | 1488748 A1 | | 12/2004 | WO | WO 2005/055950 A1 | 6/2005 |
| EP | 1712252 A1 | | 10/2006 | WO | WO 2005/058294 A1 | 6/2005 |
| EP | 1738760 A1 | | 1/2007 | WO | WO 2005/065079 A2 | 7/2005 |
| EP | 1832302 A1 | | 9/2007 | WO | WO 2005/077347 | 8/2005 |
| EP | 1223981 B1 | | 1/2008 | WO | WO 2005/082341 A2 | 9/2005 |
| FR | 2812551 A1 | | 2/2002 | WO | WO 2005/089778 A1 | 9/2005 |
| FR | 2899479 A1 | | 10/2007 | WO | WO 2005/110505 A2 | 11/2005 |
| GB | 692578 | | 6/1953 | WO | WO 2005/117755 A2 | 12/2005 |

| | | |
|---|---|---|
| WO | WO 2005/123170 A1 | 12/2005 |
| WO | WO 2006/005939 A1 | 1/2006 |
| WO | WO 2006/019844 A1 | 2/2006 |
| WO | WO 2006/020180 A2 | 2/2006 |
| WO | WO 2006/028836 A1 | 3/2006 |
| WO | WO 2006/031922 A2 | 3/2006 |
| WO | WO 2006/055940 A2 | 5/2006 |
| WO | WO 2006/059237 A1 | 6/2006 |
| WO | WO 2006/063350 A2 | 6/2006 |
| WO | WO 2007/008927 A2 | 1/2007 |
| WO | WO 2007/014285 A2 | 2/2007 |
| WO | WO 2007/015964 A1 | 2/2007 |
| WO | WO 2007/019439 A2 | 2/2007 |
| WO | WO 2007/056316 A2 | 5/2007 |
| WO | WO 2007/060433 A1 | 5/2007 |
| WO | WO 2007/067621 A2 | 6/2007 |
| WO | WO 2007/067623 A2 | 6/2007 |
| WO | WO 2007/067625 A2 | 6/2007 |
| WO | WO 2007/067637 A2 | 6/2007 |
| WO | WO 2007/082331 A1 | 7/2007 |
| WO | WO 2007/084610 A2 | 7/2007 |
| WO | WO 2007/111925 A2 | 10/2007 |
| WO | WO 2007/124132 A2 | 11/2007 |
| WO | WO 2007/133618 A2 | 11/2007 |
| WO | WO 2007/133644 A2 | 11/2007 |
| WO | WO 2007/142683 A2 | 12/2007 |
| WO | WO 2008/006658 A1 | 1/2008 |
| WO | WO 2008/036361 A2 | 3/2008 |
| WO | WO 2008/048481 A2 | 4/2008 |
| WO | WO 2008/049029 A2 | 4/2008 |
| WO | WO 2008/063943 A2 | 5/2008 |
| WO | WO 2008/080128 A1 | 7/2008 |
| WO | WO 2008/086397 A2 | 7/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greet, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cell Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1998, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, Managing Draining Wounds and Fistulae: "New and Established Methods," Chronic Wound Care, edited by D. Krasner (Health Management Publications, Inc., King of Prussia, PA 1990), pp. 240-246.
G. Živadinović, V. Dukić, Ž. Maksimović, D. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Response filed Jun. 29, 2011 for U.S. Appl. No. 12/828,117.
Notice of Allowance date mailed Aug. 26, 2011 for U.S. Appl. No. 12/828,117.
Response filed Aug. 16, 2011 for U.S. Appl. No. 10/161,076.
PCT International Search Report and Written Opinion Issued on Jul. 16, 2008 in PCT International Application No. PCT/US 08/00596.
Non-Final Office Action dated Nov. 19, 2003 for U.S. Appl. No. 10/075,743.
Response filed Mar. 9, 2006 for U.S. Appl. No. 10/075,743.
Final Office Action dated Jun. 2, 2004 for U.S. Appl. No. 10/075,743.
Response filed Nov. 23, 2004 for U.S. Appl. No. 10/075,743.
Non-Final Office Action dated Dec. 16, 2004 for U.S. Appl. No. 10/075,743.
Response filed Apr. 18, 2005 for U.S. Appl. No. 10/075,743.
Notice of Allowance dated Jun. 27, 2005 for U.S. Appl. No. 10/075,743.
RCE/Response filed Jan. 9, 2006 for U.S. Appl. No. 10/075,743.
Notice of Allowance date mailed Jan. 20, 2006 for U.S. Appl. No. 10/075,743.
Non-Final Office Action dated Sep. 14, 2007 for U.S. Appl. No. 11/409,116.
Response filed Jan. 8, 2008 for U.S. Appl. No. 11/409,116.
Final Office Action dated Mar. 27, 2008 for U.S. Appl. No. 11/409,116.
Response filed Apr. 11, 2008 for U.S. Appl. No. 11/409,116.
Advisory Action before the Filing of an Appeal Brief dated Jun. 2, 2008 for U.S. Appl. No. 11/409,116.
Notice of Allowance dated Apr. 14, 2009 for U.S. Appl. No. 11/409,116.
Request for Continued Examination filed on Jun. 4, 2009 for U.S. Appl. No. 11/409,116.
Non-Final Office Action dated Sep. 3, 2009 for U.S. Appl. No. 11/409,116.
Examiners Interview Summary dated Dec. 29, 2009 for U.S. Appl. No. 11/409,116.
Response filed Dec. 31, 2009 for U.S. Appl. No. 11/409,116.
Notice of Allowance date mailed Feb. 17, 2010 for U.S. Appl. No. 11/409,116.
Non-Final Office Action dated Oct. 1, 2008 for U.S. Appl. No. 11/657,887.
Response filed Dec. 22, 2008 for U.S. Appl. No. 11/657,887.
Non-Final Action dated Jun. 23, 2009 for U.S. Appl. No. 11/657,887.
Response filed Sep. 18, 2009 for U.S. Application No. 11/657,887.
Notice of Allowance dated Dec. 11, 2009 for U.S. Appl. No. 11/657,887.
Non-Final Office Action dated Dec. 3, 2003 for U.S. Appl. No. 10/161,076.
Response filed Jun. 2, 2004 for U.S. Appl. No. 10/161,076.
RCE filed Sep. 28, 2004 for U.S. Appl. No. 10/161,076.
Final Office Action dated Dec. 15, 2004 for U.S. Appl. No. 10/161,076.
RCE and response filed Jun. 15, 2005 for U.S. Appl. No. 10/161,076.
Non-Final Office Action dated Sep. 7, 2005 for U.S. Appl. No. 10/161,076.
Response filed Mar. 7, 2006 for U.S. Appl. No. 10/161,076.
Final Office Action dated May 24, 2006 for U.S. Appl. No. 10/161,076.
RCE and response filed Nov. 21, 2006 for U.S. Appl. No. 10/161,076.
Non-Final Office Action dated Feb. 12, 2007 for U.S. Appl. No. 10/161,076.
Non-Final Office Action dated Sep. 14, 2007 for U.S. Appl. No. 10/161,076.
Response filed Mar. 14, 2008 for U.S. Appl. No. 10/161,076.
Final Office Action dated Jun. 20, 2008 for U.S. Appl. No. 10/161,076.
Notice of Appeal filed Dec. 22, 2008 for U.S. Appl. No. 10/161,076.
Request for Continued Examination and Amendment filed Jul. 22, 2009 for U.S. Appl. No. 10/161,076.
Non-Final Action dated Aug. 25, 2009 for U.S. Appl. No. 10/161,076.
Response Filed Feb. 25, 2010 for U.S. Appl. No. 10/161,076.
Re-Submission filed Mar. 15, 2010 of Feb. 25, 2010 Response to Office Action for U.S. Appl. No. 10/161,076.
Final Rejection date mailed Apr. 8, 2010 for U.S. Appl. No. 10/161,076.
RCE/Response filed Oct. 8, 2010 for U.S. Appl. No. 10/161,076.
Final Office Action date mailed Oct. 25, 2010 for U.S. Appl. No. 10/161,076.
Letter withdrawing Official Action date mailed Nov. 3, 2010 for U.S. Appl. No. 10/161,076.
Response filed Jan. 7, 2011 for U.S. Appl. No. 10/161,076.
Non-Final Office Action date mailed Feb. 16, 2011 for U.S. Appl. No. 10/161,076.
Non-Final Office Action date mailed Mar. 9, 2011 for U.S. Appl. No. 12/828,117.

* cited by examiner

711 ⇒

```
┌─────────────────────────────────────────┐
│ POSITIONING A MULTI-LAYER REDUCED PRESSURE │
│ DELIVERY APPARATUS IN CONTACT WITH A TISSUE │──715
│ SITE, THE APPARATUS HAVING A SCAFFOLD, A │
│ HYDROGEL-FORMING POLYMER, AND A MANIFOLD │
└─────────────────────────────────────────┘
                    ↓
┌─────────────────────────────────────────┐
│ ORIENTING THE APPARATUS SUCH THAT THE    │──719
│ SCAFFOLD CONTACTS THE TISSUE SITE        │
└─────────────────────────────────────────┘
                    ↓
┌─────────────────────────────────────────┐
│ APPLYING A REDUCED PRESSURE TO THE TISSUE│──723
│ SITE THROUGH THE MANIFOLD AND THE SCAFFOLD│
└─────────────────────────────────────────┘
```

```
┌─────────────────────────────────────────┐
│ POSITIONING A SCAFFOLD IN CONTRACT WITH A │
│ TISSUE SITE, A HYDROGEL-FORMING POLYMER IN│──815
│ CONTACT WITH THE SCAFFOLD, AND A MANIFOLD IN│
│ CONTACT WITH THE HYDROGEL-FORMING POLYMER │
└─────────────────────────────────────────┘
                    ↓
┌─────────────────────────────────────────┐
│ STIMULATING NEW TISSUE GROWTH AT THE TISSUE│
│ SITE BY APPLYING A REDUCED PRESSURE TO THE│──819
│ TISSUE SITE THROUGH THE MANIFOLD AND THE │
│                SCAFFOLD                  │
└─────────────────────────────────────────┘
```

FIG. 8

BIOCOMPATIBLE WOUND DRESSING

CROSS-REFERENCE TO RELATED APPLICATIONS

This application is a continuation of U.S. patent application Ser. No. 11/657,887 filed on Jan. 25, 2007, now U.S. Pat. No. 7,700,819 which is a continuation-in-part of U.S. patent application Ser. No. 11/409,116, filed on Apr. 21, 2006, now U.S. Pat. No. 7,763,769 which is a continuation of U.S. patent application Ser. No. 10/075,743 filed on Feb. 14, 2002, now U.S. Pat. No. 7,070,584, which claims the benefit of and priority to U.S. Provisional Application No. 60/269,657, filed Feb. 16, 2001. All of the above-mentioned applications are hereby incorporated by reference.

BACKGROUND OF THE INVENTION

1. Field of the Invention

This invention relates generally to a system or method of promoting tissue growth and more specifically to a multi-layer wound dressing having a tissue growth medium for enhancing the growth of tissue when exposed to reduced pressure.

2. Description of Related Art

Vacuum induced healing of open wounds has recently been popularized by Kinetic Concepts, Inc. of San Antonio, Tex., by its commercially available V.A.C.® product line. The vacuum induced healing process has been described in commonly assigned U.S. Pat. No. 4,969,880 issued on Nov. 13, 1990 to Zamierowski, as well as its continuations and continuations in part, U.S. Pat. No. 5,100,396, issued on Mar. 31, 1992, U.S. Pat. No. 5,261,893, issued Nov. 16, 1993, and U.S. Pat. No. 5,527,293, issued Jun. 18, 1996, the disclosures of which are incorporated herein by this reference. Further improvements and modifications of the vacuum induced healing process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, the disclosures of which are incorporated by reference as though fully set forth herein.

Substantial work has also been performed relating to the creation of bioabsorbable and includable, cell growth enhancing matrices, lattices, or scaffolds. Exemplary U.S. patents known to applicant include Kemp et al. U.S. Pat. No. 5,256,418 issued Oct. 26, 1993; Chatelier et al. U.S. Pat. No. 5,449,383 issued Sep. 12, 1995; Bennett et al. 5,578,662 issued Nov. 26, 1996; and two patents issued to Yasukawa et al. U.S. Pat. No. 5,629,186 issued May 13, 1997 and U.S. Pat. No. 5,780,281 issued Jul. 14, 1998, both from a common parent application; the disclosures of which are incorporated by reference herein.

As is well known to those of ordinary skill in the art, closure of surface wounds involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion; thereafter, cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but also are less able to successfully fight bacterial infection and thus are less able to naturally close the wound. Until the advent of vacuum induced therapy, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples may cause very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative gauge pressure, commercialized by Assignee or its parent under the designation "Vacuum Assisted Closure" (or "V.A.C.®") therapy, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return.

While V.A.C.® therapy has been highly successful in the promotion of wound closure, healing many wounds previously thought largely untreatable, some difficulty remains. Because the very nature of V.A.C.® therapy dictates an atmospherically sealed wound site, the therapy must often be performed to the exclusion of other beneficial, and therefore desirable, wound treatment modalities. One of these hitherto excluded modalities is the encouragement of cell growth by the provision of an in situ cell growth-enhancing matrix.

Additional difficulty remains in the frequent changing of the wound dressing. As the wound closes, binding of cellular tissue to the wound dressing may occur. Use of traditional V.A.C.® therapy necessitates regular changing of the dressing. Reckless dressing changes can result in some tissue damage at the wound site if cellular tissue has grown excessively into the dressing.

SUMMARY

The problems presented by existing tissue dressings are solved by the systems and methods of the present invention. In accordance with one embodiment of the present invention, a reduced pressure delivery system is provided for applying reduced pressure tissue treatment to a tissue site. The reduced pressure delivery system includes a multi-layer reduced pressure delivery apparatus having a tissue contact layer, a release layer, and a manifold layer. The tissue contact layer includes a scaffold adapted to contact the tissue site. The release layer includes a water-soluble polymer and a plurality of flow channels, and the manifold layer includes a distribution manifold. The release layer is positioned between the tissue contact layer and the manifold layer, and the water-soluble polymer of the release layer binds to at least one of the tissue contact layer and the manifold layer. A reduced-pressure delivery tube is fluidly connected to the manifold layer to deliver a reduced pressure to the tissue site.

In accordance with another embodiment of the present invention, a multi-layer reduced pressure delivery apparatus includes a first layer having a scaffold adapted to contact a tissue site and a second layer having a water-soluble polymer and a plurality of flow channels. The water-soluble polymer contacts the scaffold. The reduced pressure delivery apparatus further includes a third layer having a distribution manifold contacting the water-soluble polymer.

In still another embodiment of the present invention, a multi-layer reduced pressure delivery apparatus includes a tissue contact, a manifold layer, and a release layer. The tissue contact layer includes a scaffold adapted to contact the tissue site to receive in-growth of new tissue from the tissue site. The tissue contact layer further includes a first plurality of flow channels. The manifold layer includes a cellular material and a third plurality of flow channels, the cellular material being capable of distributing a reduced pressure to the tissue site. The release layer is positioned between the tissue contact layer and the manifold layer and includes a water-soluble polymer connected to at least one of the tissue contact layer and the manifold layer. The water-soluble polymer is adapted to dissolve following hydration by a fluid to release the at least one of the tissue contact layer and the manifold layer. The release layer further includes a second plurality of flow channels in fluid communication with the first and third plurality of flow channels.

Also in accordance with the present invention, another embodiment of the reduced pressure delivery system includes a reduced pressure delivery apparatus having a distribution manifold, a scaffold, and a water-soluble polymer. The distribution manifold distributes a reduced pressure, and the scaffold encourages in-growth of new tissue from a tissue site. The distribution manifold and scaffold are bound together by the water-soluble polymer, which is positioned between the distribution manifold and the scaffold. The system further includes a reduced-pressure delivery tube having a distal end fluidly connected to the distribution manifold to deliver the reduced pressure through the distribution manifold and scaffold to the tissue site.

Other objects, features, and advantages of the present invention will become apparent with reference to the drawings and detailed description that follow.

BRIEF DESCRIPTION OF THE DRAWINGS

FIG. 7 illustrates a method of promoting new tissue growth at a tissue site according to one embodiment of the present invention;

FIG. 8 depicts a method of promoting new tissue growth at a tissue site according to another embodiment of the present invention.

DETAILED DESCRIPTION OF THE PREFERRED EMBODIMENT

Figure 1:
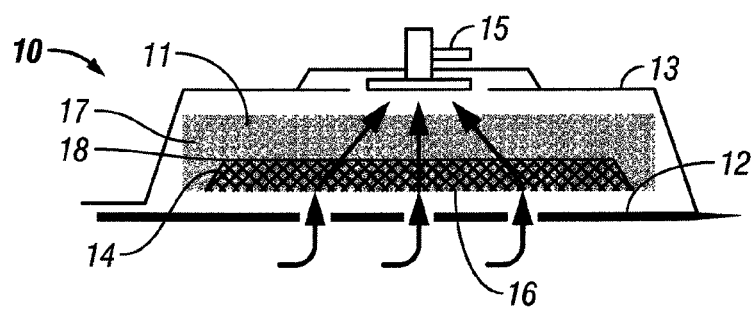
FIG. 1 illustrates a partially cut away perspective view of a wound dressing according to an embodiment of the present invention, the wound dressing being shown applied to a tissue site.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The term "manifold" as used herein generally refers to a substance or structure that is provided to assist in applying reduced pressure to, delivering fluids to, or removing fluids from a tissue site. A manifold typically includes a plurality of flow channels or pathways that are interconnected to improve distribution of fluids provided to and removed from the area of tissue around the manifold. Examples of manifolds may include without limitation devices that have structural elements arranged to form flow channels, cellular foam such as open-cell foam, porous tissue collections, and liquids, gels and foams that include or cure to include flow channels.

The term "reduced pressure" as used herein generally refers to a pressure less than the ambient pressure at a tissue site that is being subjected to treatment. In most cases, this reduced pressure will be less than the atmospheric pressure at which the patient is located. Although the terms "vacuum" and "negative pressure" may be used to describe the pressure applied to the tissue site, the actual pressure applied to the tissue site may be significantly less than the pressure normally associated with a complete vacuum. Reduced pressure may initially generate fluid flow in the tube and the area of the tissue site. As the pressure around the tissue site approaches the desired reduced pressure, the flow may subside, and the reduced pressure is then maintained. Unless otherwise indicated, values of pressure stated herein are gage pressures.

The term "scaffold" as used herein refers to a substance or structure used to enhance or promote the growth of cells and/or the formation of tissue. A scaffold is typically a three dimensional porous structure that provides a template for cell growth. The scaffold may be infused with, coated with, or comprised of cells, growth factors, extracellular matrix components, nutrients, integrins, or other substances to promote cell growth. A scaffold may be used as a manifold in accordance with the embodiments described herein to administer reduced pressure tissue treatment to a tissue site.

The term "tissue site" as used herein refers to a wound or defect located on or within any tissue, including but not limited to, bone tissue, adipose tissue, muscle tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The present invention is a biocompatible wound dressing for use with negative pressure therapy. The term "wound" as used herein, may include burns, incisional wounds, excisional wounds, ulcers, traumatic wounds, and chronic open wounds. As used herein, the term "pad" refers to foam, screens, other porous-like materials. The term "conventional pad" refers to polyurethane (PU) or polyvinylalcohol (PVA) foams commonly used with V.A.C.® therapy. The term "V.A.C.® therapy" as used herein, refers to negative pressure wound therapy as commercialized by the assignee or its parent, and further described in the aforementioned patents and patent applications.

Referring now to the figures, the present invention 10 is shown to generally comprise a foam pad 11 for insertion substantially into the wound site 12 and a wound drape 13 for sealing enclosure of the foam pad 11 at the wound site 12. According to the invention, the foam pad 11 is modified to contain a cell growth-enhancing matrix, or lattice 14, whereby a desired highly porous cell growth enhancing substrate may be directed into and about the wound site 12. After insertion into the wound site 12 and sealing with the wound drape 13, the foam pad 11 is placed in fluid communication with a vacuum source for promotion of fluid drainage, as known to those of ordinary skill in the art. Foam pad 11 is modified from prior art pads in that the pad 11 comprises matrix 14 that is noninvasive to the known V.A.C.® therapy and therefore requires no modification thereof.

According to the preferred embodiment of the present invention, the foam pad 11, wound drape 13 and vacuum source are implemented as known in the prior art, with the exception of those modifications to the foam pad 11 detailed further herein. Each of these components is detailed in U.S. patent application Ser. No. 08/951,832 filed Oct. 16, 1997, which is a Continuation of U.S. patent application Ser. No. 08/517,901 filed Aug. 22, 1995, which is a Continuation-in-part of U.S. patent application Ser. No. 08/293,854 filed Aug. 22, 1994. By this reference, the full specification of U.S. patent application Ser. No. 08/951,832 ("the '832 application"), including the claims and the drawings, is incorporated as though fully set forth herein.

As detailed in the '832 application, the foam pad 11 preferably comprises a highly reticulated, open-cell polyurethane or polyether foam for good permeability of wound fluids while under suction. As also detailed in the '832 application, the foam pad 11 is preferably placed in fluid communication, via a plastic or like material hose 15, with a vacuum source, which preferably comprises a canister safely placed under vacuum through fluid communication, via an interposed hydrophobic membrane filter, with a vacuum pump. Finally, the '832 application also details the wound drape 13, which preferably comprises an elastomeric material at least peripherally covered with a pressure sensitive, acrylic adhesive for sealing application over the wound site 12.

According to the preferred method of the present invention, those components as are described in the '832 application are generally employed as known in the art with the exception that the foam pad 11 is provided with a matrix 14. This matrix 14 is shown to comprise porous material 16 that has been formed into a plurality of sections 17. The material 16 is implanted in the foam pad 11 at the base 18 of the pad 11. Because it is necessary to trim the foam pad 11 in preparation for V.A.C.® therapy wound treatment, material 16 preferably is placed in the central portion of pad 11. Applicant does not intend to limit itself to a regular or symmetrical arrangement of material 16 or sections 17 by use of the term "matrix".

Alternatively, or in addition to the preferred embodiment, the foam pad may be comprised of bioabsorbable branched polymers alone (not shown), or in combination with the matrix 14.

Upon placement of the pad 11, having the matrix 14 embedded therein, and/or protruding therefrom, and/or comprised of bioabsorbable branched polymers, the wound drape 13 is applied over the pad to form an airtight seal over the wound site. In use, the V.A.C.® therapy is conducted as known and, if desired, cell growth enhancement therapy is added by simply providing the matrix 14 comprising material 16. In this manner, cell growth enhancement therapy may be conveniently combined with existing V.A.C.® therapies, without loss of V.A.C.® therapy performance and without inconvenience or overly increased cost.

EXAMPLE I

The above described open celled foam is formed into a pad. The general principles set forth in U.S. Pat. No. 5,795,584 issued to Totakura et al on Aug. 18, 1998 at Col. 5 lines 5 42, are followed to create a structure superimposed on the bottom of the pad. Holes are placed in those portions of the non-bioabsorbable substrate relatively remote from the bioabsorbable cell growth enhancing matrix substrate. The matrix covers a portion of the pad located within the boundaries of the wound being treated. The pad is then completely covered by an airtight drape, and subjected to sub atmospheric pressure, as is the standard practice for utilizing V.A.C.® therapy. The matrix is absorbed within the expected useful life of the pad, so, that when the pad is removed, the matrix had been absorbed, and the growing cells are not disturbed. The pad is replaced, if necessary, either by a conventional pad or by a matrix containing pad, as deemed therapeutically necessary.

EXAMPLE II

A conventional pad is selected. A collagen cell growth matrix is applied to a portion of the bottom thereof. The general principles of V.A.C.® therapy are followed, with the matrix containing pad substituted for a conventional pad. During the expected duty cycle of the pad, the collagen matrix is absorbed by the growing cells, so that when the pad is removed, the matrix had been absorbed, and the growing cells are not disturbed. The pad is replaced, if necessary, either by a conventional pad or by a matrix containing pad, as deemed therapeutically necessary.

EXAMPLE III

The procedure set forth in EXAMPLE II is followed. However, an ultra-low density fused-fibrous ceramic, sometimes referred to under the trademark P.R.I.M.M., is substituted for the collagen matrix thereof. The general principles of V.A.C.® therapy are followed. During the expected duty cycle of the pad, the ultra-low density fused-fibrous ceramic is absorbed by the growing cells, so that when the pad is removed, the ultra-low density fused-fibrous ceramic had been absorbed, and the growing cells were not disturbed. The pad is replaced, if necessary, either by a conventional pad or by a matrix containing pad, as deemed therapeutically necessary.

EXAMPLE IV

Many suitable bioabsorbable materials have been used for sutures, surgical implements, and the like. A small sample of these materials are set forth in the following U.S. patents, to wit: U.S. Pat. No. 5,997,568, issued to Lin on Dec. 7, 1999 and the following patents issued in 1999 to Roby et al.: U.S. Pat. Nos. 5,914,387; 5,902,874 and 5,902,875. A selected one or more of these, or similar materials, are placed upon a conventional pad. The general principles of V.A.C.® therapy are followed. During the expected duty cycle of the pad, the bioabsorbable material is absorbed by the growing cells, so, that when the pad is removed, the bioabsorbable material had been absorbed, and the growing cells were not disturbed. The pad is replaced, if necessary, either by a conventional pad or by a matrix containing pad, as deemed therapeutically necessary.

EXAMPLE V

A bioabsorbable branched polymer, similar to that described in U.S. Pat. No. 5,578,662 issued to Bennet et al., forms the pad. The general principles of V.A.C.® therapy are followed with the bioabsorbable branched polymer pad substituted for the conventional pad. During the expected duty cycle of the pad, the pad is absorbed by the growing cells, so that there is no need to replace the pad and disturb the wound site. If further treatment is deemed necessary, a conventional pad, or an additional matrix containing pad, or an additional bioabsorbable branched polymer pad may be placed in the wound site, and V.A.C.® therapy continued.

Figure 2:
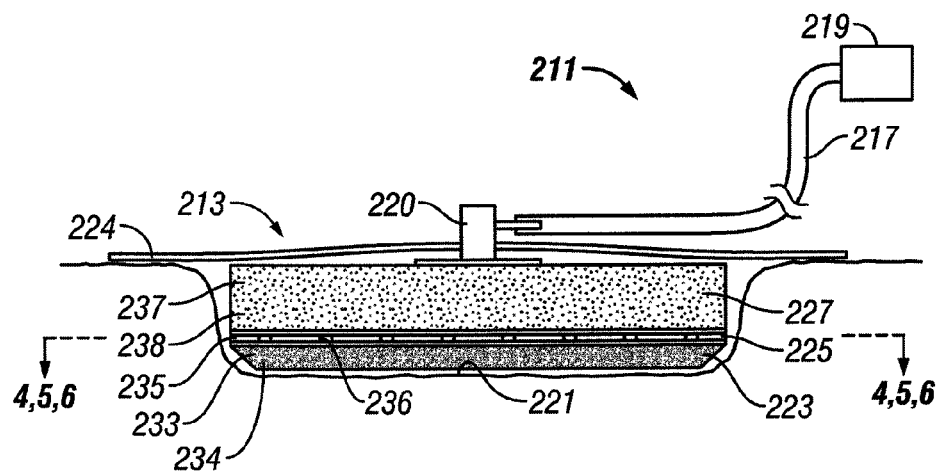
FIG. 2 depicts a cross-sectional side view of a reduced pressure delivery system according to an embodiment of the present invention, the system including a reduced pressure delivery apparatus having a tissue contact layer, a release layer, and a manifold layer.
Figure 3:
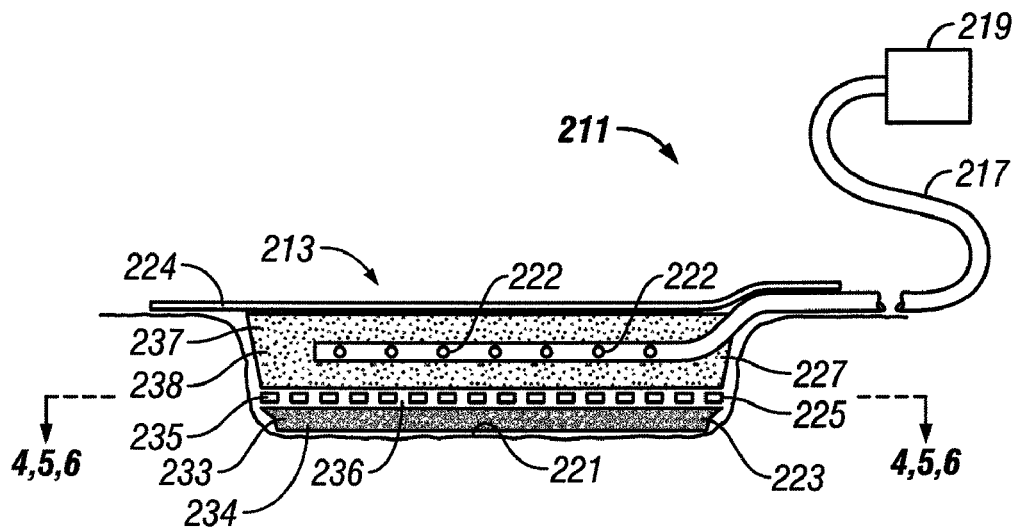
FIG. 3 illustrates a cross-sectional side view of a reduced pressure delivery system according to an embodiment of the present invention, the system including a reduced pressure delivery apparatus having a tissue contact layer, a release layer, and a manifold layer.

Referring to FIGS. 2 and 3, a reduced pressure delivery system 211 according to an embodiment of the present invention includes a biocompatible wound or tissue dressing, or reduced pressure delivery apparatus, 213, a reduced pressure delivery tube 217, and a reduced pressure source 219. The reduced pressure delivery system 211 is provided to administer a reduced pressure tissue treatment to a tissue site 221 of a person. The tissue site may include a burn or other wound, or alternatively may be healthy tissue upon which it is desired to promote new tissue growth. The reduced pressure source 219 is fluidly connected to a distal end of the reduced pressure delivery tube 217, and the reduced pressure delivery apparatus 213 is fluidly connected to a proximal end of the reduced pressure delivery tube 217. In FIG. 2, the reduced pressure delivery tube 217 is fluidly connected to the reduced pressure delivery apparatus 213 by a tubing connector 220 similar to that illustrated in FIG. 1. In FIG. 3, the reduced pressure delivery tube 217 is placed directly inside or adjacent to the reduced pressure delivery apparatus 213 and may include a plurality of apertures 222 for communicating with the reduced pressure delivery apparatus 213. The reduced pressure source delivers a reduced pressure through the reduced pressure delivery tube 217 to the reduced pressure delivery apparatus 213, and the reduced pressure delivery apparatus 213 distributes the reduced pressure to the tissue site 221. A membrane 224 is positioned over the reduced pressure delivery apparatus 213 and sealingly connected to the tissue surrounding the tissue site 221. The membrane 224 reduces contamination of the tissue site 221 and assists in maintaining the reduced pressure at the tissue site 221.

The reduced pressure delivery apparatus 213 is a multi-layer apparatus having a first layer, or tissue contact layer 223, a second layer, or release layer 225, and a third layer, or manifold layer 227. The first layer 223 includes a scaffold 233 and a first plurality of flow channels 234. The second layer 225 includes a release material 235 such as a hydrogel-forming material or a water-soluble polymer. The second layer 225 further includes a second plurality of flow channels 236. The third layer 227 includes a distribution manifold 237 and a third plurality of flow channels 238. The three layers are arranged such that the second layer 225 is positioned between the first layer 223 and the third layer 227, the first layer 223 being adjacent to the second layer 225, the second layer 225 being adjacent to the first and third layers 223, 227, and the third layer 227 being adjacent to the second layer 225.

In one embodiment, each of the layers 223, 225, 227 is connected to adjacent layers by any connection means appropriate for the type of material in each layer. For example, the third layer 227 may be bonded to the second layer 225, or the first layer 223 may be bonded to the second layer 225, or all three layers 223, 225, 227 may be bonded together. Bonding may be accomplished by heating one, both, or all of the layers at their interface and applying a force to press the layers into a bonded connection. Alternatively, adhesives or mechanical fasteners may be used to connect the layers to one another as long as the fastening or bonding means does not substantially and negatively affect the distribution of pressure through the layers. In another embodiment, the layers 223, 225, 227 may not be connected to one another, but rather, the layers 223, 225, 227 may simply be placed in contact with one another prior to and/or during application of the reduced pressure tissue treatment. Alternatively, two of the layers may be bonded to one another, and a third of the layers placed in contact with one of the two bonded layers. For example, the second layer 225 may be connected to the third layer 227 in a way described previously, and the first layer 223 may be placed in contact with, but not connected to, the second layer 225. Instead, the second layer 225 may be connected to the first layer 223, and the second layer 225 may be placed in contact with, but not connected to, the third layer 227.

The first, second, and third plurality of flow channels 234, 236, 238 are provided in the first, second, and third layers 223, 225, 227, respectively, to allow distribution of reduced pressure within the reduced pressure delivery apparatus 213 and to the tissue site 221. The flow channels provided in each layer may be an inherent characteristic of the material provided in that layer (e.g. a naturally porous material), or the flow channels may be chemically, mechanically, or otherwise formed in the material prior to or after assembly of the three layers 223, 225, 227. The placement of the layers 223, 225, 227 adjacent to one another allows the flow channels in one layer to fluidly communicate with the flow channels in the adjacent layer. For example, the relative positioning or connection of the layers as described above allow the first plurality of flow channels 234 to fluidly communicate with the second plurality of flow channels 236, which are capable of fluidly communicating with the third plurality of flow channels 238.

The scaffold 233 of the first layer, or tissue contact layer, 223 promotes new tissue growth and accepts in-growth of new tissue from the tissue site 221. The scaffold 223 may be any porous, bioresorbable material that is capable of accepting and/or integrating new tissue growth into the scaffold. The pores of the scaffold 233 are preferably interconnected to define the first plurality of flow channels 234, but additional flow channels may be provided by mechanically, chemically, or otherwise forming the flow channels within the scaffold. Suitable scaffold materials may include, without limitation, polylactic acid (PLA), polyglycolic acid (PGA), polycaprolactone, polyhydroxybutyrate, polyhydroxyvalerate, polydioxanone, polyorthoesthers, polyphosphazenes, polyurethanes, collagen, hyaluronic acid, chitosan, and copolymers, terpolymers, or blends of these materials. Additional materials, which may be used with hard tissue applications include, but are not limited to, ceramics such as hydroxyapatite, coralline apatite, calcium phosphate, calcium sulfate, calcium carbonate or other carbonates, bioglass, allografts, autografts, and composites of these ceramics with the previously listed polymeric materials. The scaffold material may further include a polymeric blend of PLA, PGA, polycarbonates, polyfumarates, capralactones, and/or any of the above-mentioned materials. The scaffold 233 may be manufactured by any of the following processes: salt leaching, freeze-drying, phase-separation, weaving fibers, bonding non-woven fibers, foaming, or any other suitable manufacturing method for the selected material.

The pore sizes associated with the scaffold 233 are typically between about 50 and 500 microns, and more preferably between about 100 and 400 microns. Pore sizes below 50 microns tend to inhibit or prevent tissue growth. In one embodiment, the preferred average pore size of pores within the scaffold is about 100 microns.

The scaffold may be provided as a sheet or pad of material. The thickness of the scaffold is measured in a direction normal to the tissue site when the reduced pressure delivery apparatus is placed adjacent the tissue site. The thickness of the material may vary, but in one embodiment the scaffold is about 1 to 4 mm in thickness. The dimensions of the sheet or pad of scaffold material in a plane normal to the thickness dimension may vary depending on the size of the tissue site to be treated. The pad or sheet of material may be provided in a large size and then trimmed to fit the tissue site.

The release material 235 of the second layer, or release layer, 225 minimizes points of contact between the first layer 223 and the third layer 227. In one embodiment, the release material 235 will prevent any contact between the first and third layers 223, 227. By minimizing contact between the first and second layers 223, 227, the release material 235 serves as a barrier to tissue in-growth from the scaffold 233 into the distribution manifold 237 of the third layer 227.

The release material 235 also serves as a binder and a release agent for the first and third layers 223, 227. Prior to and during reduced pressure tissue treatment, the release material 235 may be used to bind the first and third layers as previously described. The release material 235 is preferably either a hydrogel-forming material or a water-soluble polymer.

As a hydrogel-forming material, the release material 235 is capable of forming a liquid and/or gel following exposure to water or other fluids. During initial application of the reduced pressure delivery apparatus 213 to the tissue site and during the administration of reduced pressure tissue treatment, the hydrogel-forming material is preferably in a solid, "non-hydrated" state. In other words, the hydrogel-forming material has not yet transformed into a liquid and/or gel-like state. As reduced pressure tissue treatment is administered, the hydrogel-forming material may be exposed to wound exudate and other fluids being drawn from or administered to the tissue site, but the compression of the first, second, and third layers under the influence of the reduced pressure preferably reduces or eliminates the absorption of fluids by the hydrogel-forming material. This allows the hydrogel-forming material to remain in a solid state until reduced pressure delivery is ceased. Following cessation of reduced pressure therapy, the hydrogel-forming material may be hydrated by either applying water, saline solution, or other fluids to the hydrogel-forming material or by allowing wound exudate to hydrate the hydrogel-forming material. As the hydrogel-forming material hydrates, the material transforms into a liquid and/or gel state which allows easy release of the third layer 227 from the first layer 223.

The hydrogel-forming material may be any suitable material that is capable of accepting and/or forming a liquid or gel-like substance after exposure to water or other fluids for a specified period of time. The hydrogel-forming material is typically a cross-linked polymer; however, it is not required that the material be cross-linked. Suitable hydrogel-forming materials may include, without limitation, cross-linked polyethylene glycol, hydrophilic polyethers, polyvinyl alcohol, polyvinyl acetate, polyacrylates, polysulfonates, polyphosphazene hydrogels, collagen, gelatin, hyaluronic acid, glucosaminoglycans, chitosan, and alginate. Uncrosslinked polymers with hydrophobic and hydrophilic portions may also be used, such as a copolymer of ethylene glycol and lactic acid or a polyurethane with a very long hydrophilic soft segment.

The release material 235 may also be a water-soluble polymer. As a water-soluble polymer, the release material 235 is capable of dissolving in the presence of water or other liquids. During initial application of the reduced pressure delivery apparatus 213 to the tissue site and during the administration of reduced pressure tissue treatment, the water-soluble polymer is preferably in a "non-hydrated" form. In other words, the polymer has not yet absorbed water or other liquids. As reduced pressure tissue treatment is administered, the water-soluble polymer may be exposed to wound exudate and other fluids being drawn from or administered to the tissue site, but the compression of the first, second, and third layers under the influence of the reduced pressure preferably reduces the solubility of the water-soluble polymer, which prevents the water-soluble polymer from prematurely dissolving. This allows the water-soluble polymer to remain in a solid state until reduced pressure delivery is ceased. Following cessation of reduced pressure therapy, the water-soluble polymer may be hydrated by either applying a fluid to the polymer or by allowing wound exudate to hydrate the polymer. As the water-soluble polymer hydrates, the polymer dissolves into the hydrating liquid which allows easy release of the third layer 227 from the first layer 223.

The water-soluble polymer may include, without limitation, uncrosslinked polyethylene glycol, hydrophilic polyethers, polyvinyl alcohol, polyvinyl acetate, polyacrylates, polysulfonates, polyphosphazenes, collagen, hyaluronic acid, glucosaminoglycans, chitosan, and deoxyribonucleic acid (DNA).

Figure 4:
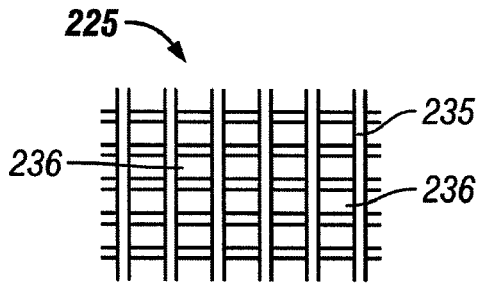
FIG. 4 depicts a top view of one embodiment of the release layer of FIGS. 2 and 3 taken at 4-4.
Figure 5:
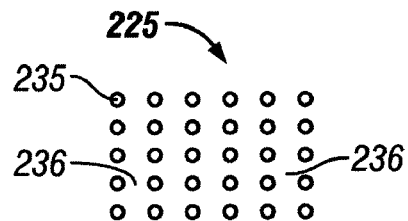
FIG. 5 illustrates a top view of another embodiment of the release layer of FIGS. 2 and 3 taken at 5-5.

The presence of the second plurality flow channels 236 in the second layer 225 allows the distribution of reduced pressure from the distribution manifold 237 to the scaffold 233. The second plurality of flow channels 236 further allow passage of any fluids being provided to or being removed from the tissue site 221. While the second plurality of flow channels 236 may be an inherent characteristic of the release material 235 (i.e. interconnected pores or other flow channels within the material itself), it is more likely that the second plurality of flow channels 236 are mechanically, chemically, or otherwise formed in the release material 235. For example, referring to FIG. 4, the second plurality of flow channels 236 may be defined by voids between adjacent strands of release material 235 arranged in a grid-like pattern. Alternatively, referring to FIG. 5, the release material 235 may be applied as beads of material between the first and third layers 223, 227. In this particular configuration, the second plurality of flow channels 236 is defined by voids between adjacent beads of the release material 235. In still another configuration, referring to FIG. 6, a sheet of the release material 235 may be provided with apertures formed in the sheet to define the second plurality of flow channels 236. The shape, size, and positioning of the apertures and voids described above could vary, and in one embodiment, may be random.

Regardless of whether pores, voids, apertures, or some combination thereof are used to define the second plurality of flow channels 236, the porosity of the second layer 225 may be less than the porosity of the scaffold 233 to minimize in-growth of tissue into the second layer 225. The porosity of the second layer 225 may be controlled by limiting the size of the pores, voids, or apertures, or by controlling the number (i.e. density) of pores, voids, or apertures disposed in the second layer 225. The porosity of the second layer 225, however, must remain high enough to allow distribution of reduced pressure and the flow of fluids through the second layer 225.

Figure 6:
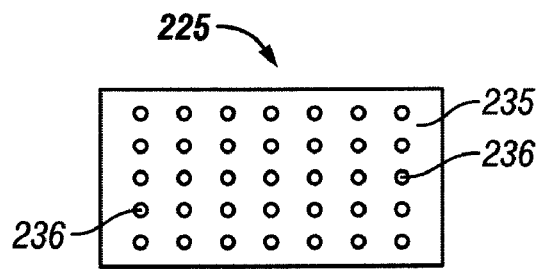
FIG. 6 depicts a top view of still another embodiment of the release layer of FIGS. 2 and 3 taken at 6-6.

Like the scaffold 233, the release material 235 may be provided as a sheet or pad of material (see FIG. 6). Alternatively, the release material 235 may be provided in grids of strands, dots, or other individual pieces of material (see FIGS. 4 and 5). The shape, size, and distribution of these individual pieces of material may vary and in some situations, the shape, size, and distribution may be random. The thickness of the release material 235 is measured in a direction normal to the tissue site when the reduced pressure delivery apparatus is placed adjacent the tissue site. Although not required, the thickness of the release material 235 is typically less than the thickness of the scaffold to save money on material costs. In one embodiment, the thickness of the release material 235 is about 200 to 500 microns prior to absorption of fluid. Following the hydration of the release material, the thickness may swell to about 500 micros to 1 millimeter. The dimensions of the sheet or pad of release material in a plane normal to the thickness dimension may vary depending on the size of the tissue site to be treated, but will typically be about the same size in length and width as that of the scaffold. The pad or sheet of material may be provided in a large size and then trimmed to fit the tissue site.

The distribution manifold 237 of the third layer, or manifold layer 227 assists in distributing reduced pressure received from the reduced pressure delivery tube 217. The manifold may further be used to distribute fluids that are introduced to the tissue site or to manifold wound exudate and other fluids collected from the tissue site. The manifold 237 may be any porous material that is capable of accomplishing these tasks, and in one embodiment, the manifold is formed from a cellular material such as an open-cell foam. The material preferably includes cells that are fluidly connected to adjacent cells. The third plurality of flow channels 238 is formed by and between the "open cells" of the cellular material. The flow channels allow fluid communication throughout that portion of the cellular material having open cells. The cells and flow channels may be uniform in shape and size, or may include patterned or random variations in shape and size. Variations in shape and size of the cells of the cellular material result in variations in the third plurality of flow channels 238, and such characteristics can be used to alter the flow characteristics of fluid through the cellular material. The cellular material may further include portions that include "closed cells." These closed-cell portions of the cellular material contain a plurality of cells, the majority of which are not fluidly connected to adjacent cells. Closed-cell portions of cellular material may be selectively combined with open-cell portions to prevent transmission of fluids through selected portions of the manifold 237.

In one embodiment, the manifold 237 is made from an open-cell, reticulated polyetherurethane foam with pore sizes ranging from about 400-600 microns. An example of this foam may include GranuFoam manufactured by Kinetic Concepts, Inc. of San Antonio, Tex. The manifold 237 may also be polyurethane foam, polyvinyl alcohol foam, polyethylene foam, expanded polytetrafluoroethylene, silicone foam, loofa sponge, sea sponge, gauze, felted mats, or any other biocompatible material that is capable of providing fluid communication through a plurality of flow channels in three dimensions.

Like the scaffold 233 and the release material 235, the manifold 237 may be formed from a sheet or pad of material. The thickness of the manifold 237 may vary, but in one embodiment, the thickness will be at least as great as the thickness of the scaffold 233. The dimensions of the manifold in a plane normal to the thickness dimension may also vary depending on the size of the tissue site being treated. The pad or sheet of manifold material may be provided in a large size and then trimmed to fit the tissue site.

In operation, the reduced pressure delivery apparatus 213 is trimmed if necessary to match the shape and size of the tissue site 221. In many cases, the tissue site 221 may be an open wound, burn, or other-damaged tissue, but the tissue site 221 may similarly be a site that contains healthy tissue upon which it is desired to grow additional tissue. The reduced pressure delivery apparatus 213 is placed adjacent the tissue site 221 such that the first layer 223 is in contact with the tissue site 221. As previously described, the multiple layers of the reduced pressure delivery apparatus 213 may be laminated, bonded, or otherwise connected, but the layers may also be separate from one another. If certain of the layers are not connected to one another, the various layers may be placed individually such that the first layer 223 is in contact with the tissue site, the second layer 225 is in contact with the first layer 223, and the third layer 227 is in contact with the second layer 225.

After positioning the reduced pressure delivery apparatus 213, a reduced pressure is delivered from the reduced pressure source 219 through the reduced pressure delivery tube 217 to the manifold 237 of the first layer 227. The reduced pressure is distributed through the third plurality of flow channels 238 associated with the manifold 237 to the second plurality of flow channels 236 associated with the second layer 225. The reduced pressure is then distributed to the first plurality of flow channels 234 associated with the scaffold 233 of the first layer 223. As reduced pressure reaches the tissue site 221, fluids at the tissue site 221 such as wound exudate may be drawn through the first, second, and third plurality of flow channels 234, 236, 238 and removed from the reduced pressure delivery apparatus 213. A reservoir (not shown) and various filters may be provided between the reduced pressure delivery apparatus 213 and the reduced pressure source 219 to collect exudate and protect the reduced pressure source 219. In addition to allowing distribution of reduced pressure and the withdrawal of fluids from the tissue site 221, the first, second, and third plurality of flow channels 234, 236, 238 may be used to distribute fluids such as irrigation fluids, medication, antimicrobials, antibacterials, antivirals, and growth factors to the tissue site 221.

The application of reduced pressure to the tissue site 219 induces new tissue growth. Some of the mechanisms by which new tissue growth is promoted include mircro-deformation of the tissue, epithelial migration, and improved blood flow. These factors contribute to increasing the development of granulation tissue at the tissue site, which results in new tissue growth. While the discussion of providing reduced pressure tissue treatment often refers to "delivering" reduced pressure to the tissue site, it should be apparent to a person of ordinary skill in the art that delivery of reduced pressure typically involves creating a pressure differential between the reduced pressure source 219 and the tissue site 221. The pressure differential (with a lower pressure at the reduced pressure source 219 than at the tissue site 221) creates an initial fluid flow from the tissue site 221 toward the reduced pressure source 219. Once the pressure at the tissue site 221 nears or equals that of the pressure at the reduced pressure source 219, the reduced pressure may be maintained at the tissue site due to the fluid connection with the reduced pressure source 219 and the sealing function of the membrane 224.

As new tissue forms under the influence of reduced pressure, the new tissue is permitted to grow into the scaffold 233. The material chosen for the scaffold 233 preferably supports and encourages new tissue growth. Since the scaffold will remain at the tissue site following the administration of reduced pressure tissue treatment, it is preferred that new tissue penetrates the scaffold as much as possible. It has been observed that under the influence of reduced pressure, new tissue may penetrate up to 1 mm (thickness) of scaffold in a period of two days. Since the thickness of the scaffold 233 in some embodiments may only be about 1 to 4 mm, it may be desired to remove the second and third layers 225, 227 of the reduced pressure delivery apparatus 213 and replace the layers with a new dressing containing first, second, and third layers 223, 225, 227. In other words, a new scaffold 233 may be placed on top of the old scaffold 233 following removal of the second and third layers 225, 227. By removing only a portion of the reduced pressure delivery apparatus 213 and leaving the scaffold 233, it is possible to incrementally add new tissue growth to the tissue site 221 as new scaffolds 233 are stacked upon previously inserted scaffolds 233 that are already permeated with new tissue growth.

The release of the second and third layers 225, 227 from the first layer 223 is simplified by the presence of the release material 235. During the application of reduced pressure and removal of fluids from the tissue site 221, the release material 235 preferably remains in a solid state, thereby allowing the second plurality of flow channels 236 to remain open. While the release material will typically transform into a liquid or gel or will dissolve following the absorption of water or other fluids, this change is significantly reduced during the application of reduced pressure to the reduced pressure delivery apparatus 213. Reduced pressure results in a compression of the reduced pressure delivery apparatus 213, which reduces the surface area of the release material that is exposed to fluids flowing through the first, second, and third plurality of flow channels 234, 236, 238. Absorption of fluids by the release material 235 is thereby minimized until reduced pressure delivery is ceased.

During the application of reduced pressure, the release material preferably minimizes or prevents contact between the first and third layers 223, 227. New tissue growing into the scaffold 233 is hindered from growing in the manifold 237 by this separation between the scaffold 233 and manifold 237 and by the release material 235 itself. While tissue growth into the manifold 237 may still occur, the growth is minimized, which lessens pain to the patient upon removal of the manifold 237.

Following application of reduced pressure for a selected period of time, the release material may be hydrated by soaking the reduced pressure delivery apparatus 213 with water, saline solution, or other fluids. Alternatively, the reduced pressure delivery apparatus 213 may be allowed to sit until bodily fluids from the tissue site hydrate the release material 235. If the release material 235 is a hydrogel-forming material, the release material 235 transforms into a gel-like state and typically expands as it hydrates. This allows for easier removal of the manifold 237 from the scaffold 233. Any hydrogel-forming material (or hydrogel) that remains following removal of the manifold 237 may be manually removed or dissolved by the introduction of additional fluids. Alternatively, if the release material 235 is a water-soluble polymer, it will be dissolved as it absorbs water or other fluids, thus releasing the third layer 227 from the first layer 223.

Referring to FIG. 7, a method 711 of promoting tissue growth at a tissue site according to an embodiment of the present invention is illustrated. The method 711 includes positioning a multi-layer reduced pressure delivery apparatus in contact with the tissue site at 715. The reduced pressure delivery apparatus includes a scaffold, a release material, and a manifold. At 719, the apparatus is oriented such that the scaffold contacts the tissue site. A reduced pressure is applied to the tissue site through the manifold and the scaffold at 723.

Referring to FIG. 8, a method 811 of promoting new tissue growth at a tissue site according to an embodiment of the present invention is illustrated. The method 811 includes at 815 positioning a scaffold in contact with the tissue site, a release material in contact with the scaffold, and a manifold in contact with the release material. At 819, new tissue growth is stimulated at the tissue site by applying a reduced pressure to the tissue site through the manifold and the scaffold.

Figure 9:
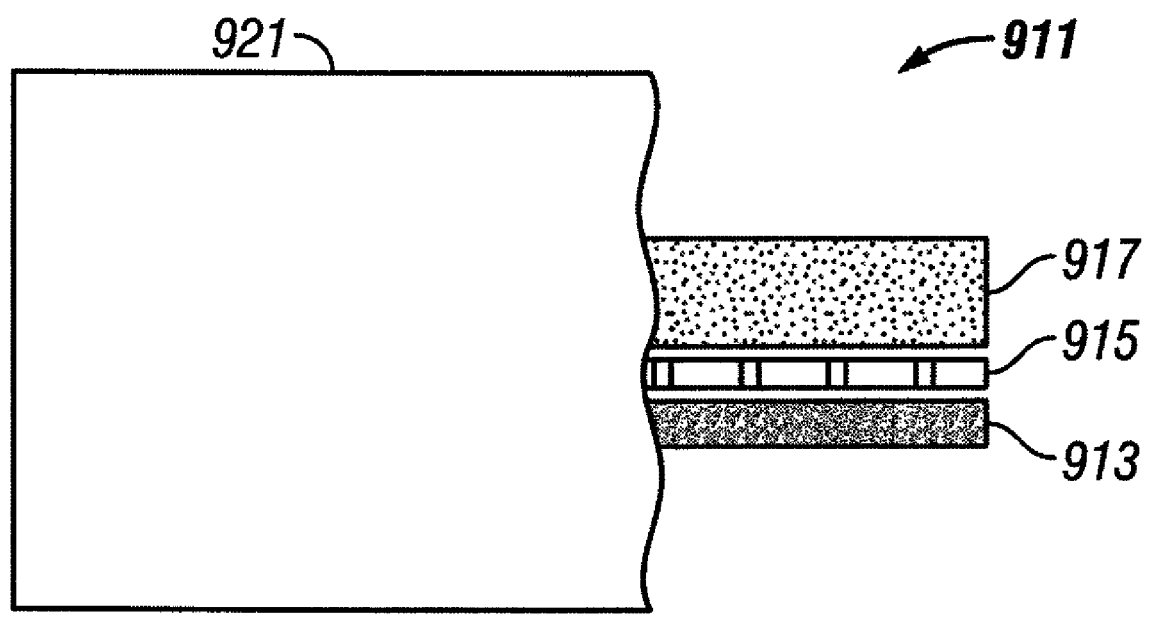
FIG. 9 illustrates front view of a tissue growth kit according to an embodiment of the present invention.

Referring to FIG. 9, a tissue growth kit 911 for promoting new tissue growth at a tissue site according to an embodiment of the present invention includes a scaffold 913, a release material 915, and a distribution manifold 917. The scaffold 913 includes a first and second side, the first side of the scaffold 913 being adapted to contact the tissue site. The scaffold 913 is similar to the scaffold 233 described previously with reference to FIGS. 2 and 3. The release material 915 is adapted to contact the second side of the scaffold 913 and is similar to the release material 235 described previously with reference to FIGS. 2 and 3. The distribution manifold 917 is adapted to contact the release material 915 to distribute a reduced pressure to the tissue site through the scaffold 913. The distribution manifold 917 is similar to the manifold 237 described previously with reference to FIGS. 2 and 3. The tissue growth kit 911 may further include a container 921 for housing the scaffold 913, release material 915, and distribution manifold 917 prior to use of the components. The container 921 may be a flexible bag, a box, or any other container suitable for storing the scaffold 913, release material 915, and distribution manifold 917.

While the multi-layer reduced pressure delivery apparatus disclosed herein is used in conjunction with a reduced pressure delivery source to provide reduced pressure tissue treatment to a tissue site, the reduced pressure delivery apparatus could also serve as an advanced tissue dressing alone in the absence of reduced pressure application. The same materials, relative positioning, and connectivity between layers may be used in the advanced tissue dressing. Similar to the reduced pressure delivery apparatus described herein, the advanced tissue dressing may include a first layer to promote and accept growth of new tissue, a third layer to assist in directing fluids away from the tissue site, and a second layer to facilitate removal of the third layer from the first layer at a selected time. The third layer of the advanced tissue dressing, instead of having a "manifold", may be considered to include a fluid reservoir for collecting and holding fluids exuded by the wound. The materials described herein as being suitable distribution manifold materials are similarly suitable materials for the reservoir of the third layer. The only requirement of the reservoir is that it be made from a material that is capable of storing fluids produced by or present at the tissue site.

While the systems and methods of the present invention have been described with reference to tissue growth and healing in human patients, it should be recognized that these systems and methods for applying reduced pressure tissue treatment can be used in any living organism in which it is desired to promote tissue growth or healing. Similarly, the systems and methods of the present invention may be applied to any tissue, including without limitation bone tissue, adipose tissue, muscle tissue, dermal tissue, vascular tissue, connective tissue, cartilage, tendons, or ligaments. While the healing of tissue may be one focus of applying reduced pressure tissue treatment as described herein, the application of reduced pressure tissue treatment may also be used to generate tissue growth in tissues that are not diseased, defective, or damaged. For example, it may be desired to apply reduced pressure tissue treatment to grow additional tissue at a tissue site that can then be harvested. The harvested tissue may be transplanted to another tissue site to replace diseased or damaged tissue, or alternatively the harvested tissue may be transplanted to another patient.

It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure delivery system for applying reduced pressure tissue treatment to a tissue site comprising:
    a multi-layer reduced pressure delivery apparatus having a tissue contact layer, a release layer, and a manifold layer, the tissue contact layer including a scaffold adapted to contact the tissue site, the release layer including a water-soluble polymer and a plurality of flow channels, the manifold layer including a distribution manifold, the release layer being positioned between the tissue contact layer and the manifold layer, the water-soluble polymer of the release layer binding to at least one of the tissue contact layer and the manifold layer; and
    a reduced-pressure delivery tube fluidly connected to the manifold layer to deliver a reduced pressure to the tissue site.

2. The reduced pressure delivery system according to claim 1, wherein the water-soluble polymer is positioned between the scaffold and the distribution manifold to substantially prevent contact between the scaffold and the distribution manifold in areas where the water-soluble polymer is disposed.

3. The reduced pressure delivery system according to claim 2, wherein the distribution manifold contacts the scaffold in areas in which the water-soluble polymer is not disposed during application of the reduced pressure.

4. The reduced pressure delivery system according to claim 1, wherein the tissue contact layer is from about 1 mm to about 4 mm in thickness.

5. The reduced pressure delivery system according to claim 1, wherein the thickness of the release layer is less than the thickness of the tissue contact layer.

6. The reduced pressure delivery system according to claim 1, wherein the plurality of flow channels of the release layer are provided by pores disposed in a sheet of the water-soluble polymer.

7. The reduced pressure delivery system according to claim 6, wherein the pore sizes of the pores in the release layer are less than the pore sizes of the pores in the scaffold.

8. The reduced pressure delivery system according to claim 1, wherein:
    the water-soluble polymer is arranged in a grid pattern such that strands of the water-soluble polymer are aligned in rows and columns; and
    the plurality of flow channels are formed by voids disposed between the rows and columns of the water-soluble polymer.

9. The reduced pressure delivery system according to claim 1, wherein:
    the water-soluble polymer is provided as a plurality of individual beads, each bead being spaced apart from adjacent beads by a void; and
    the plurality of flow channels are formed by the voids disposed between the beads of the water-soluble polymer.

10. The reduced pressure delivery system according to claim 9, wherein the porosity provided by the voids is less than the porosity provided by the scaffold.

11. The reduced pressure delivery system according to claim 1, wherein the distribution manifold is an open-cell, reticulated polyurethane foam.

12. The reduced pressure delivery system according to claim 1, wherein the water-soluble polymer is a barrier to tissue penetration.

13. The reduced pressure delivery system according to claim 1, wherein the scaffold is comprised of at least one material selected from the group of polylactic acid polyglycolic acid, polycaprolactone, polyhydroxybutyrate, polyhydroxyvalerate, polydioxanone, polyorthoesthers, polyphosphazenes, polyurethanes, collagen, hyaluronic acid, chitosan, hydroxyapatite, coralline apatite, calcium phosphate, calcium sulfate, calcium carbonate, bioglass, allografts, and autografts.

14. The reduced pressure delivery system according to claim 1, wherein the water-soluble polymer is comprised of at least one material selected from the group of uncrosslinked polyethylene glycol, hydrophilic polyethers, polyvinyl alcohol, polyvinyl acetate, polyacrylates, polysulfonates, polyphosphazenes, collagen, hyaluronic acid, glucosaminoglycans, chitosan, and deoxyribonucleic acid (DNA).

15. The reduced pressure delivery system according to claim 1, wherein the distribution manifold is comprised of at least one material selected from the group of polyurethane foam, polyvinyl alcohol foam, polyethylene foam, expanded polytetrafluoroethylene, silicone foam, loofa sponge, sea sponge, gauze, and felted mats.

16. The reduced pressure delivery system according to claim 1 further comprising:
    a reduced pressure source fluidly connected to a proximal end of the reduced-pressure delivery tube.

17. A multi-layer reduced pressure delivery apparatus for applying reduced pressure tissue treatment to a tissue site comprising:
    a first layer having a scaffold adapted to contact a tissue site;
    a second layer having a water-soluble polymer and a plurality of flow channels, the water-soluble polymer contacting the scaffold; and a third layer having a distribution manifold contacting the water-soluble polymer.

18. The reduced pressure delivery apparatus according to claim 17, wherein the water-soluble polymer is positioned between the first layer and the third layer and is connected to at least one of the scaffold and the distribution manifold.

19. The reduced pressure delivery apparatus according to claim 17 further comprising:
a reduced-pressure delivery tube fluidly connected to the third layer to deliver a reduced pressure to the tissue site.

20. The reduced pressure delivery apparatus according to claim 17, wherein the water-soluble polymer is positioned between the scaffold and the distribution manifold to substantially prevent contact between the scaffold and the distribution manifold in areas where the water-soluble polymer is disposed.

21. The reduced pressure delivery apparatus according to claim 17, wherein the distribution manifold contacts the scaffold in areas in which the water-soluble polymer is not disposed during application of a reduced pressure.

22. The reduced pressure delivery apparatus according to claim 17, wherein a reduced pressure is delivered to the tissue site through the distribution manifold, the plurality of flow channels, and the scaffold.

23. The reduced pressure delivery apparatus according to claim 17, wherein the flow channels are capable of transmitting a fluid from the scaffold to the distribution manifold during the application of a reduced pressure.

24. The reduced pressure delivery apparatus according to claim 23, wherein the fluid is a wound exudate from the tissue site.

25. The reduced pressure delivery apparatus according to claim 17, wherein the first layer is from about 1 mm to about 4 mm in thickness.

26. The reduced pressure delivery apparatus according to claim 17, wherein the thickness of the second layer in a dehydrated state is less than the thickness of the first layer.

27. The reduced pressure delivery apparatus according to claim 17, wherein the scaffold includes pores having pore sizes ranging from about 50 microns to about 500 microns in diameter.

28. The reduced pressure delivery apparatus according to claim 17, wherein the scaffold includes pores having pore sizes ranging from about 100 microns to about 400 microns in diameter.

29. The reduced pressure delivery apparatus according to claim 17, wherein the plurality of flow channels of the second layer are provided by pores disposed in a sheet of the water-soluble polymer.

30. The reduced pressure delivery apparatus according to claim 29, wherein the pore sizes of the pores in the second layer are less than the pore sizes of the pores in the scaffold.

31. The reduced pressure delivery apparatus according to claim 17, wherein:
the water-soluble polymer is arranged in a grid pattern such that strands of the water-soluble polymer are aligned in rows and columns; and
the plurality of flow channels are formed by voids disposed between the rows an columns of the water-soluble polymer.

32. The reduced pressure delivery apparatus according to claim 17, wherein:
the water-soluble polymer is provided as a plurality of individual beads, each bead being spaced apart from adjacent beads by a void; and
the plurality of flow channels are formed by the voids disposed between the beads of the water-soluble polymer.

33. The reduced pressure delivery apparatus according to claim 32, wherein the porosity provided by the voids is less than the porosity provided by the scaffold.

34. The reduced pressure delivery apparatus according to claim 17, wherein the distribution manifold is a cellular foam.

35. The reduced pressure delivery apparatus according to claim 17, wherein the distribution manifold is an open-cell, reticulated polyurethane foam.

36. The reduced pressure delivery apparatus according to claim 17, wherein the distribution manifold includes pore sizes ranging from about 400 to about 600 microns in diameter.

37. The reduced pressure delivery apparatus according to claim 17, wherein the third layer includes an antimicrobial agent.

38. The reduced pressure delivery apparatus according to claim 17, wherein the water-soluble polymer is bioabsorbable.

39. The reduced pressure delivery apparatus according to claim 17, wherein the water-soluble polymer is a barrier to tissue penetration.

40. The reduced pressure delivery apparatus according to claim 17, wherein the tissue site is comprised of tissue selected from the group of adipose tissue, bone tissue, cartilage, connective tissue, dermal tissue, ligaments, muscle tissue, tendons, and vascular tissue.

41. The reduced pressure delivery apparatus according to claim 17, wherein the scaffold is comprised of at least one material selected from the group of polylactic acid, polyglycolic acid, polycaprolactone, polyhydroxybutyrate, polyhydroxyvalerate, polydioxanone, polyorthoesthers, polyphosphazenes, polyurethanes, collagen, hyaluronic acid, chitosan, hydroxyapatite, coralline apatite, calcium phosphate, calcium sulfate, calcium carbonate, bioglass, allografts, and autografts.

42. The reduced pressure delivery apparatus according to claim 17, wherein the water-soluble polymer is comprised of at least one material selected from the group of uncrosslinked polyethylene glycol, hydrophilic polyethers, polyvinyl alcohol, polyvinyl acetate, polyacrylates, polysulfonates, polyphosphazenes, collagen, hyaluronic acid, glucosaminoglycans, chitosan, and deoxyribonucleic acid (DNA).

43. The reduced pressure delivery apparatus according to claim 17, wherein the distribution manifold is comprised of at least one material selected from the group of polyurethane foam, polyvinyl alcohol foam, polyethylene foam, expanded polytetrafluoroethylene, silicone foam, loofa sponge, sea sponge, gauze, and felted mats.

44. The reduced pressure delivery apparatus according to claim 17, wherein the distribution manifold is chosen from the group of a woven porous pad, a non-woven porous pad, a loofa sponge, and a sea sponge.

45. A multi-layer reduced pressure delivery apparatus for applying reduced pressure tissue treatment to a tissue site comprising:
a tissue contact layer having a scaffold adapted to contact the tissue site to receive in-growth of new tissue from the tissue site, the tissue contact layer further having a first plurality of flow channels;
a manifold layer having a cellular material to distribute a reduced pressure to the tissue site, the manifold layer further having a third plurality of flow channels; and
a release layer positioned between the tissue contact layer and the manifold layer, the release layer including a water-soluble polymer connected to at least one of the tissue contact layer and the manifold layer, the water-soluble polymer adapted to dissolve following hydration by a fluid to release the at least one of the tissue contact layer and the manifold layer, the release layer further having a second plurality of flow channels in fluid communication with the first and third plurality of flow channels.

46. The reduced pressure delivery apparatus according to claim 45 further comprising a reduced-pressure delivery tube fluidly connected to the manifold layer to deliver the reduced pressure to the tissue site through the third plurality of flow channels, the second plurality of flow channels, and the first plurality of flow channels.

47. The reduced pressure delivery apparatus according to claim 45, wherein:
the water-soluble polymer substantially prevents contact between the scaffold and the cellular material in areas where the water-soluble polymer is disposed; and
the cellular material contacts the scaffold in areas in which the water-soluble polymer is not disposed during application of the reduced pressure.

48. The reduced pressure delivery apparatus according to claim 45, wherein the tissue contact layer is from about 1 mm to about 4 mm in thickness.

49. The reduced pressure delivery apparatus according to claim 45, wherein the thickness of the release layer is less than the thickness of the tissue contact layer.

50. The reduced pressure delivery apparatus according to claim 45, wherein the scaffold includes pores having pore sizes ranging from about 50 microns to about 500 microns in diameter.

51. The reduced pressure delivery apparatus according to claim 45, wherein the second plurality of flow channels of the release layer are provided by pores disposed in a sheet of the water-soluble polymer.

52. The reduced pressure delivery apparatus according to claim 51, wherein the pore sizes of the pores in the release layer are less than the pore sizes of the pores in the scaffold.

53. The reduced pressure delivery apparatus according to claim 45, wherein:
the water-soluble polymer is arranged in a grid pattern such that strands of the water-soluble polymer are aligned in rows and columns; and
the second plurality of flow channels are formed by voids disposed between the rows and columns of the water-soluble polymer.

54. The reduced pressure delivery apparatus according to claim 45, wherein:
the water-soluble polymer is provided as a plurality of individual beads, each bead being spaced apart from adjacent beads by a void; and
the second plurality of flow channels are formed by the voids disposed between the beads of the water-soluble polymer.

55. The reduced pressure delivery apparatus according to claim 54, wherein the porosity provided by the voids is less than the porosity provided by the scaffold.

56. The reduced pressure delivery apparatus according to claim 45, wherein the cellular material is an open-cell, reticulated polyurethane foam.

57. The reduced pressure delivery apparatus according to claim 45, wherein the water-soluble polymer is a barrier to tissue penetration.

58. The reduced pressure delivery apparatus according to claim 45, wherein the scaffold is comprised of at least one material selected from the group of polylactic acid, polyglycolic acid, polycaprolactone, polyhydroxybutyrate, polyhydroxyvalerate, polydioxanone, polyorthoesthers, polyphosphazenes, polyurethanes, collagen, hyaluronic acid, chitosan, hydroxyapatite, coralline apatite, calcium phosphate, calcium sulfate, calcium carbonate, bioglass, allografts, and autografts.

59. The reduced pressure delivery apparatus according to claim 45, wherein the water-soluble polymer is comprised of at least one material selected from the group of uncrosslinked polyethylene glycol, hydrophilic polyethers, polyvinyl alcohol, polyvinyl acetate, polyacrylates, polysulfonates, polyphosphazenes, collagen, hyaluronic acid, glucosaminoglycans, chitosan, and deoxyribonucleic acid (DNA).

60. The reduced pressure delivery apparatus according to claim 45, wherein the cellular material is comprised of at least one material selected from the group of polyurethane foam, polyvinyl alcohol foam, polyethylene foam, expanded polytetrafluoroethylene, silicone foam, loofa sponge, sea sponge, gauze, and felted mats.

61. A reduced pressure delivery system for applying reduced pressure tissue treatment to a tissue site comprising:
a reduced pressure delivery apparatus having a distribution manifold to distribute a reduced pressure and a scaffold to encourage in-growth of new tissue from the tissue site, the distribution manifold and scaffold being bound together by a water-soluble polymer positioned between the distribution manifold and the scaffold; and
a reduced-pressure delivery tube having a distal end fluidly connected to the distribution manifold to deliver the reduced pressure through the distribution manifold and scaffold to the tissue site.

62. The reduced pressure delivery system according to claim 61, wherein the water-soluble polymer substantially prevents contact between the scaffold and the distribution manifold in areas where the water-soluble polymer is disposed.

63. The reduced pressure delivery system according to claim 61, wherein the distribution manifold contacts the scaffold in areas in which the water-soluble polymer is not disposed during application of the reduced pressure.

64. The reduced pressure delivery system according to claim 61 further comprising:
a plurality of flow channels disposed between the scaffold and distribution manifold to allow fluid communication between the scaffold and distribution manifold.

65. The reduced pressure delivery system according to claim 61, wherein the scaffold is from about 1 mm to about 4 mm in thickness.

66. The reduced pressure delivery system according to claim 61, wherein the thickness of the water-soluble polymer is less than the thickness of the scaffold.

67. The reduced pressure delivery system according to claim 61 further comprising:
a plurality of flow channels disposed between the scaffold and distribution manifold to allow fluid communication between the scaffold and distribution manifold; and
wherein the plurality of flow channels are provided by pores disposed in a sheet of the water-soluble polymer.

68. The reduced pressure delivery system according to claim 67, wherein the pore sizes of the pores in the sheet of the water-soluble polymer are less than the pore sizes of pores in the scaffold.

69. The reduced pressure delivery system according to claim 61 further comprising:
a plurality of flow channels disposed between the scaffold and distribution manifold to allow fluid communication between the scaffold and distribution manifold;

wherein the water-soluble polymer is arranged in a grid pattern such that strands of the water-soluble polymer are aligned in rows and columns; and wherein the plurality of flow channels are formed by voids disposed between the rows and columns of the water-soluble polymer.

70. The reduced pressure delivery system according to claim 61 further comprising:

a plurality of flow channels disposed between the scaffold and distribution manifold to allow fluid communication between the scaffold and distribution manifold;

the water-soluble polymer is provided as a plurality of individual beads, each bead being spaced apart from adjacent beads by a void; and the plurality of flow channels are formed by the voids disposed between the beads of the water-soluble polymer.

71. The reduced pressure delivery system according to claim 70, wherein the porosity provided by the voids is less than the porosity provided by the scaffold.

72. The reduced pressure delivery system according to claim 61, wherein the distribution manifold is an open-cell, reticulated polyurethane foam.

73. The reduced pressure delivery system according to claim 61, wherein the water-soluble polymer is a barrier to tissue penetration.

74. The reduced pressure delivery system according to claim 61, wherein the scaffold is comprised of at least one material selected from the group of polylactic acid, polyglycolic acid, polycaprolactone, polyhydroxybutyrate, polyhydroxyvalerate, polydioxanone, polyorthoesthers, polyphosphazenes, polyurethanes, collagen, hyaluronic acid, chitosan, hydroxyapatite, coralline apatite, calcium phosphate, calcium sulfate, calcium carbonate, bioglass, allografts, and autografts.

75. The reduced pressure delivery system according to claim 61, wherein the water-soluble polymer is comprised of at least one material selected from the group of uncrosslinked polyethylene glycol, hydrophilic polyethers, polyvinyl alcohol, polyvinyl acetate, polyacrylates, polysulfonates, polyphosphazenes, collagen, hyaluronic acid, glucosaminoglycans, chitosan, and deoxyribonucleic acid (DNA).

76. The reduced pressure delivery system according to claim 61, wherein the distribution manifold is comprised of at least one material selected from the group of polyurethane foam, polyvinyl alcohol foam, polyethylene foam, expanded polytetrafluoroethylene, silicone foam, loofa sponge, sea sponge, gauze, and felted mats.

77. The reduced pressure delivery system according to claim 61 further comprising:

a reduced pressure source fluidly connected to a proximal end of the reduced-pressure delivery tube.

* * * * *